US00PP21296P2

(12) United States Plant Patent
Egger

(10) Patent No.: US PP21,296 P2
(45) Date of Patent: Sep. 14, 2010

(54) ***HEUCHERELLA* PLANT NAMED 'SWEET TEA'**

(50) Latin Name: ***Heucherella* hybrid**
Varietal Denomination: Sweet Tea

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/460,345

(22) Filed: Jul. 17, 2009

(51) Int. Cl.
*A01H 5/00* (2006.01)

(52) U.S. Cl. ..... Plt./441

(58) Field of Classification Search ..... Plt./441
See application file for complete search history.

*Primary Examiner*—Kent L Bell
(74) *Attorney, Agent, or Firm*—Klarquist Sparkman, LLP

(57) ABSTRACT

A new and distinct *Heucherella* plant substantially as shown and described, characterized by bright rose orange spring leaves with maroon along the main veins, summer color of rusty orange to rusty brown and tan with darker veins, fall and winter color of red brown with maroon veins, large, distinctive, palmately lobed leaves, large plant size, and excellent vigor.

2 Drawing Sheets

Botanical denomination: *Heucherella* hybrid.
Variety designation: 'Sweet Tea'.

BACKGROUND OF THE INVENTION

The present invention relates to a new and distinct cultivar of *Heucherella* and given the cultivar name of 'Sweet Tea'. *Heucherella* is in the family *Saxifragaceae*. *Heucherella* 'Sweet Tea' originated from a controlled cross between *Heuchera* 'V3' (a proprietary unreleased *Heuchera villosa* hybrid), as the seed parent, and massed selected *Tiarella*, as the pollen parent. The offspring were extremely variable and interesting. This is the second selected variety.

This new *Heucherella* is unique in its coloration. There are no other varieties of this coloration known to the breeder. It is distinguished by:

1. bright rose orange spring leaves with maroon along the main veins,
2. summer color of rusty orange to rusty brown and tan with darker veins,
3. fall and winter color of red brown with maroon veins,
4. large, distinctive, palmately lobed leaves,
5. large plant size, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
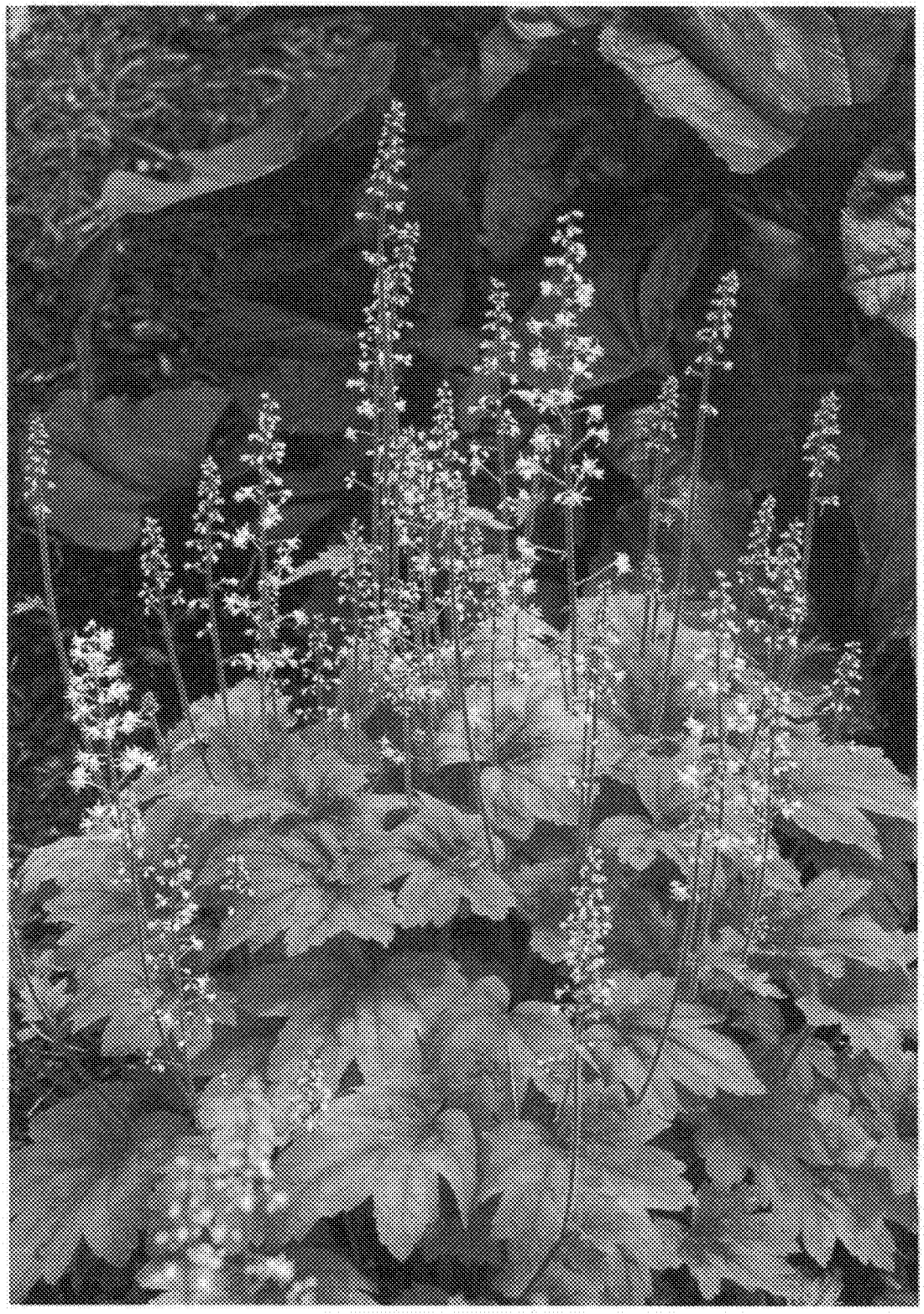
FIG. 1 shows a two year old *Heucherella* 'Sweet Tea' in bloom, growing in the garden spring in Canby, Oreg.
Figure 2:
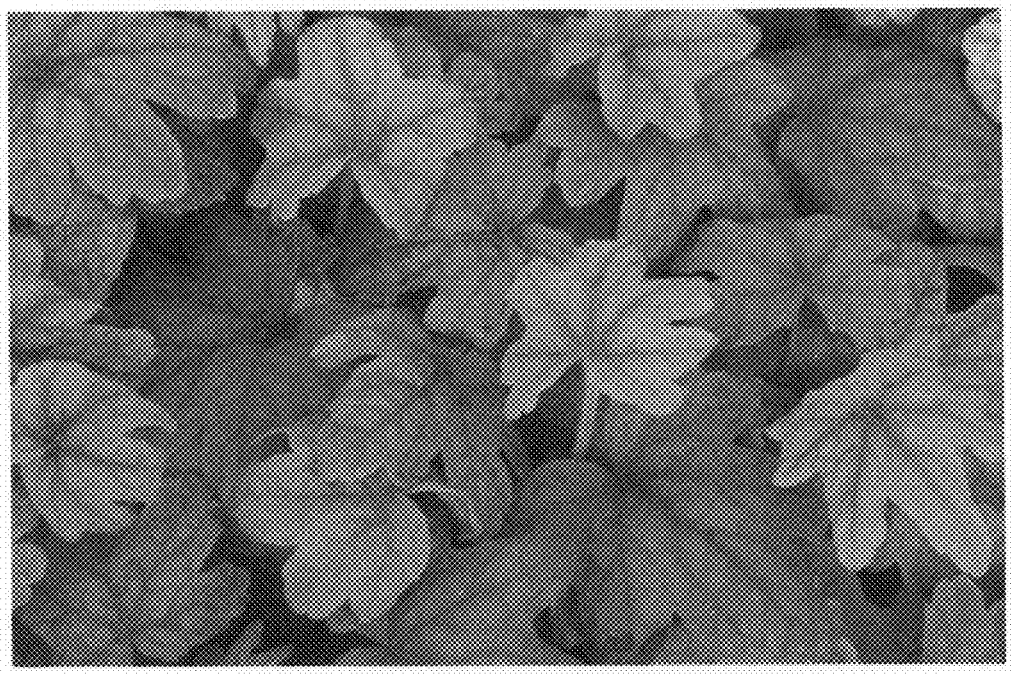
FIG. 2 shows a close up of one year old *Heucherella* 'Sweet Tea' in a flat in October in Canby, Oreg.
Figure 3:
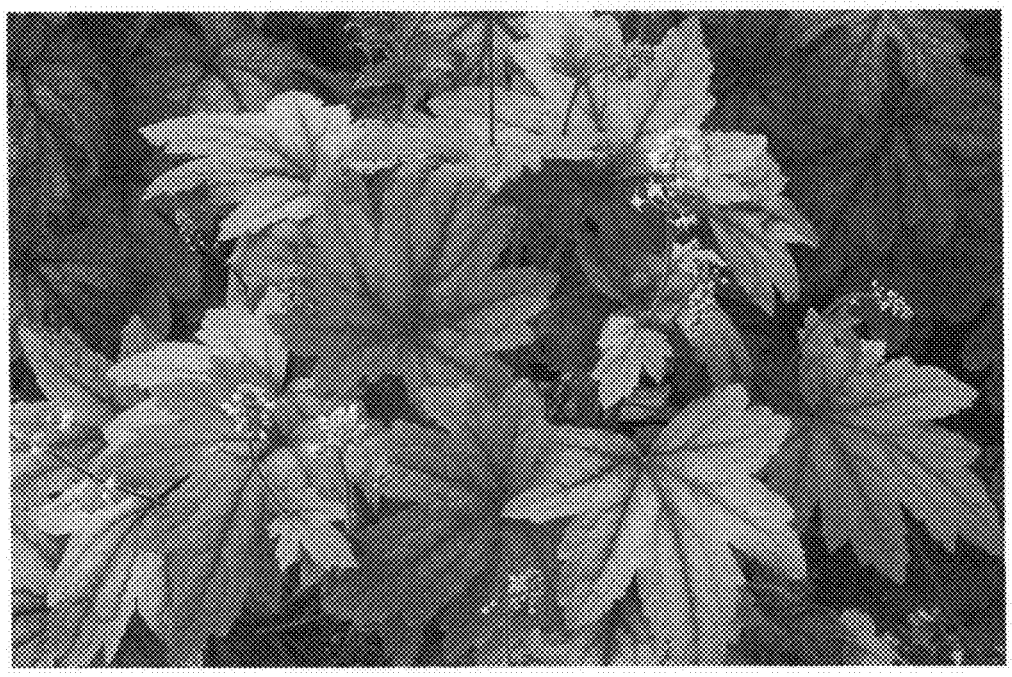
FIG. 3 shows a one year old *Heucherella* 'Sweet Tea' growing in a one gallon container under high light in spring in Canby, Oreg.

The following is a detailed description of the new *Heucherella* cultivar based on observations of a two-year-old specimen growing in a 2 gallon container in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 1999 edition.

Plant:

*Form* .—Basal rosette, herbaceous perennial.
*Hardiness.*—USDA Zone 4 to 9.
*Size.*—27 cm tall from top of the foliage to the ground and 50 cm wide.
*Habit.*—Mounding.
*Vigor.*—Excellent.
*Roots.*—Fibrous, freely branching, fine, and white in color. Roots develop easily from cuttings.

Leaf:

*Type.*—Simple.
*Arrangement.*—Rosette.
*Shape.*—Broadly ovate.
*Lobing /division* .—7 main lobes with the terminal the longest, each with secondary lobes.
*Venation.*—Palmate.
*Margins.*—Crenate.
*Apex.*—Mucronulate.
*Base.*—Cordate.
*Blade size.*—Variable, grows to 13 cm wide and 15 cm long.
*Surface texture.*—Both surfaces glandular.

*Texture.*—Thin, papery.

*Petiole description.*—Grows to 23 cm long and 3 mm wide, glandular hairs, between Greyed Orange 176A and 177B

*Leaf color.*—Extremely variable depending on light and temperature, the orange tones are most prevalent during cool temperatures; spring top side, Greyed Red 180B to Greyed Orange 172C with maroon along main veins Greyed Purple 185B, older leaves lighten to Greyed Orange 165C with the color along the veins Greyed Purple 185A; spring bottom side, Red Purple 60A; summer, fall topside Greyed Brown 175B with veins and blotch Greyed Purple 187B in shade or Greyed Orange 177A or 164C with veins and blotch Greyed Purple 187A in sun, bottom side Greyed Purple 187B.

Inflorescence:

*Size.*—Grows to 4.5 cm wide and 13.5 cm long.

*Type.*—Raceme.

*Number of flowers per raceme.*—About 50.

*Number of raceme.*—About 16.

*Peduncle.*—28 cm to 38 cm tall, 2 mm wide at base, Greyed Red 178A to Grey Brown 199B, glandular hairs, with 1 to 2 petiolate cauline leaves (ovate, blades 1.5 cm to 3 cm long and 2 cm to 3.5 cm wide with 3 to 5 lobes, no blotch, crenate, mucronate, cordate, glandular hairs, Greyed Orange 174A).

*Bloom period.*—Late May to mid June in Canby, Oreg.

*Lastingness.*—Each raceme blooms for about 2 weeks on the plant.

Flower bud:

*Size.*—2 mm wide and 3 mm long.

*Description.*—Glandular puberulent, ovoid.

*Color.*—Greyed Yellow 160C with tip Yellow Green 153A.

Flower:

*Type.*—Perfect.

*Shape.*—Campanulate.

*Size.*—10 mm wide and 6 mm deep.

*Petal description.*—5 in number, each oblanceolate, 6 mm long and 1 mm wide, tip acuminate, base attenuate, margin entire, glabrous on both sides, White 155D on both sides.

*Calyx description.*—5 mm wide and 4 mm deep, with 5 lobes, divided ¾ way to the base, campanulate, glandular hairs on outside, glabrous inside, tip obtuse, margin entire, White 155D on both sides except tips of back side which are Yellow Green 153A.

*Stamen description.*—5 in number, filaments 2.5 mm long White 155D, anthers sterile, less than 1 mm, Greyed Orange 165C.

*Pistil description.*—One central two beaked pistil, 5 mm long, White 155C.

*Fragrance.*—None.

Fruit and seed: None.

Disease and pest tolerance: No known resistance to rust, a common problem with light leaf type *Heucherella*. Excellent disease tolerance to powdery mildew. All *Heucherella* are susceptible to root weevils.

COMPARISON TO SIMILAR *HEUCHERELLA*

Compared to the seed parent, *Heuchera* 'V3' (unpatented), the new variety is lobed and more orange with a maroon blotch along the vein compared to no blotch.

Compared to the pollen parent, one of a *Tiarella* mass, the new variety has rose orange foliage in spring to rust orange in summer rather than green.

There are no similar colored *Heucherella* on the market.

I claim:

1. A new and distinct *Heucherella* plant as herein illustrated and described.

* * * * *